United States Patent [19]
Liberti et al.

[11] Patent Number: 6,120,856
[45] Date of Patent: *Sep. 19, 2000

[54] COATED, RESUSPENDABLE MAGNETICALLY RESPONSIVE, TRANSITION METAL OXIDE PARTICLES AND METHOD FOR THE PREPARATION THEREOF

[75] Inventors: Paul A. Liberti, Huntingdon Valley, Pa.; Galla C. Rao, Princeton; Joseph N. Chiarappa, Flemington, both of N.J.

[73] Assignee: Immunivest Corporation, Wilmington, Del.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/949,317

[22] Filed: Oct. 14, 1997

Related U.S. Application Data

[63] Continuation-in-part of application No. 08/482,448, Jun. 7, 1995, Pat. No. 5,698,271.

[51] Int. Cl.$^7$ .............................. H01F 1/00; B32B 5/16; C12Q 1/00; G01N 33/566
[52] U.S. Cl. .......................... 427/550; 427/221; 427/127; 427/414; 427/560; 427/598; 427/601; 428/402; 435/4; 435/7.2; 435/7.4; 435/7.7; 435/7.8; 436/501; 436/526; 436/528; 436/533; 252/62.56
[58] Field of Search .................................. 427/550, 221, 427/127, 414, 560, 598, 601; 428/402; 435/4, 7.2, 7.4, 7.7, 7.8; 436/501, 526, 528, 533; 530/363; 252/62.56

[56] References Cited

U.S. PATENT DOCUMENTS

| | | | |
|---|---|---|---|
| 3,215,572 | 11/1965 | Papell | 149/2 |
| 3,608,718 | 9/1971 | Aubrey et al. | 209/214 |
| 3,970,518 | 7/1976 | Giaever | 195/1.5 |
| 4,018,886 | 4/1977 | Giaever | 424/12 |
| 4,070,246 | 1/1978 | Kennedy et al. | 195/99 |
| 4,101,435 | 7/1978 | Hasegawa et al. | 252/62.53 |
| 4,152,210 | 5/1979 | Robinson et al. | 195/63 |
| 4,157,323 | 6/1979 | Yen et al. | 260/297 |
| 4,230,685 | 10/1980 | Senyei et al. | 424/12 |
| 4,267,234 | 5/1981 | Rembaum | 428/403 |
| 4,329,241 | 5/1982 | Massart | 252/65.52 |
| 4,335,094 | 6/1982 | Mosbach | 424/1 |
| 4,452,773 | 6/1984 | Molday | 424/1.1 |
| 4,454,234 | 6/1984 | Czerlinski et al. | 436/526 |
| 4,554,088 | 11/1985 | Whitehead et al. | 252/62.54 |
| 4,672,040 | 6/1987 | Josephson | 436/526 |
| 4,775,636 | 10/1988 | Moermans et al. | 436/518 |
| 4,795,698 | 1/1989 | Owen et al. | 436/518 |
| 5,512,332 | 4/1996 | Liberti et al. | 427/550 |
| 5,597,531 | 1/1997 | Liberti et al. | 423/57 |
| 5,698,271 | 12/1997 | Liberti et al. | 427/550 |

FOREIGN PATENT DOCUMENTS

| | | |
|---|---|---|
| 0186616 | 11/1985 | European Pat. Off. . |
| 230768 | 8/1987 | European Pat. Off. . |
| 391608 | 10/1990 | European Pat. Off. . |
| WO 83/03426 | 10/1983 | WIPO . |
| WO 88/06632 | 9/1988 | WIPO . |
| WO9102811 | 3/1991 | WIPO . |

OTHER PUBLICATIONS

J.G. Atherton and S.S. Bell, Water Res., 17: 943–948 (1983).
J.G. Atherton and S.S. Bell, Water Res., 17: 949–953.
Jane A. Langdale and Alan D.B. Malcolm, Biochemical Society Transactions, 12: 693–694 (1984).
M. Nakagaki and M. Tagawa, Yakugaku Zasshi, 99: 65–70 (1979) [Abstract in English].
Renshaw et al., Magnetic Resonance Imaging, 4: 351–357 (1986).
Kandori et al., Nippon Kagaku Kaishi, 9: 1357–1362 (1984) [Abstract in English].
Ohgushi et al., Journal of Magnetic Resonance, 29: 599–601 (1978).
Elmore The Physical Review, Vol. 54, Second Series, pp. 309–310, Jul. 1–Dec. 15, 1938.

*Primary Examiner*—Jezia Riley
*Attorney, Agent, or Firm*—Dann Dorfman Herrell and Skillman, P.C.

[57] ABSTRACT

The invention relates to an improved method for the manufacture of magnetically responsive particles, also called ferrofluids. The improved method involves a heat treatment step, which may occur at various times during the preparation of the materials, including during subdivision of the magnetic starting material, during the addion of a coating material, after formation of a magnetically responsive particle, or some combination thereof. The materials formed by such a process have numerous advantages over materials formed by other processes, including enhanced salt stability, increased coating uptake, and increased binding capacity. These ferrofluids have applications in a variety of preparative and diagnostic techniques, including immunoassay, cell separations, toxicity testing, food testing, environmental analysis, and MRI.

23 Claims, No Drawings

COATED, RESUSPENDABLE MAGNETICALLY RESPONSIVE, TRANSITION METAL OXIDE PARTICLES AND METHOD FOR THE PREPARATION THEREOF

RELATED INVENTIONS

This application is a continuation-in-part of U.S. patent application Ser. No. 08/482,448, filed Jun. 7, 1995, now U.S. Pat. No. 5,698,271, Dec. 16, 1997, the entire disclosure of which is incorporated by reference in the present specification as if set forth herein in full.

FIELD OF THE INVENTION

This invention pertains to stable suspensions of magnetic particles and to resuspendable coated magnetic particles, preferably, but not limited to, those having biochemical or biological activity, to compositions including such particles, and to methods of making and using such particles and compositions.

Biologically active magnetic particles find use in a variety of preparative and diagnostic techniques. Among these is high gradient magnetic separation (HGMS) which uses a magnetic field to separate magnetic particles from suspension. In instances where these particles are attached to biological materials of interest (e.g., cells, drugs), the material of interest or target material may thereby be separated from other materials not bound to the magnetic particles. Because of their magnetic properties, these materials also function as contrast agents for magnetic resonance imaging.

As used herein, the term "resuspendable coated particle" refers to a finely divided solid, which forms a colloidal suspension and may be separated from the suspension and subsequently resuspended. "Magnetic" encompasses material which may or may not be permanently magnetic, which also may be paramagnetic or superparamagnetic but which in all cases exhibits a response in a magnetic field, i.e., is magnetically responsive. "Disrupted" particles are those which are too small to contain a complete magnetic domain or, alternatively, whose Brownian energy exceeds their magnetic moment. Generally, these particles are less than 0.03 micron in size.

DESCRIPTION OF RELATED ART

Many techniques have been suggested in the prior art for the preparation of magnetic particles or organo-magnetic materials. Such particles generally fall into three categories: large, small and microagglomerates of small particles. Large magnetic particles, having diameters greater than 10 micron ($\mu$) respond to weak magnetic fields and magnetic field gradients. Because of their size, they tend to settle rapidly from solution and also have limited surface area per unit weight. Large particles also tend to aggregate after they have been subjected to a magnetic field because they can be permanently magnetized. Small particles which have magnetic cores of mean diameter less than $0.03\mu$ remain in solution by virtue of their Brownian energy and hence do not spontaneously settle. Microagglomerates of such small magnetic particles have been prepared by various methods. Depending on the size of the microagglomerates, materials which can remain in solution for reasonable periods of time can be prepared. Additionally, the magnetic properties of small particles and microagglomerates of small magnetic particles are significantly different from those of the larger permanently magnetizable particles. Small magnetic particles composed of either single crystals of ferromagnetic materials such as iron oxides or agglomerates of such crystals become "superparamagnetic" when the crystal size of the ferromagnetic materials is below about $0.03\mu$. Unlike ferromagnetic crystals, superparamagnetic crystals only exhibit magnetic behavior when they are in a magnetic field gradient and do not become permanently magnetized. Such materials have been referred to as dispersible magnetic metal oxide particles and also as magnetically responsive particles.

One possible route to obtaining a magnetic particle bearing a bioreceptor is that of U.S. Pat. Nos. 3,970,518 and 4,018,886 to Giaever, which teach the physical coating of such materials onto the magnetic particles via adsorption. The coating of bovine serum albumin onto $1\mu$ diameter nickel particles is exemplified.

U.S. Pat. No. 4,230,685 to Senyei et al. considers the teaching of U.S. Pat. No. 3,970,518 and states that there is "no literature verification that uncoated magnetic particles can effectively be made to bind with antibody" and presumably other bioreceptors. U.S. Pat. No. 4,554,088 to Whitehead et al. states that antibodies adsorbed on iron oxides are substantially detached by 24-hour 50° incubation in 1M sodium chloride and also that the quantity of adsorbed material is low.

With respect to one type of superparamagnetic particle described herein, namely, colloidal particles, the method of recovery proposed in U.S. Pat. Nos. 3,970,518 and 4,018, 886 could not easily be made to work on such colloidal particles, as the field strength required to capture such particles for washing away unadsorbed materials would be enormous. Additionally, a field gradient is required, which is not achievable with the apparatus there described. In conjunction with the preparative use of high gradient magnetic separation (HGMS), the concept of Giaever might work where there are effective means for adsorbing and retaining antibodies or bioreceptors on such particles.

In view of the apparent failure to produce functionally acceptable magnetic particles via bioreceptor adsorption, a number of other approaches have been pursued. These include U.S. Pat. No. 4,230,685 to Senyei et al., which discloses the preparation of microspheres containing magnetite, albumin, and protein A. The preparation taught by Senyei involves an emulsion polymerization of the above ingredients. U.S. Pat. No. 4,554,088 to Whitehead et al. teaches the silanation of magnetic metal oxides which subsequently can be covalently linked to bioactive molecules. Both of the immediately preceding approaches deal with agglomerated superparamagnetic particles; hence, the agglomerated materials are classed as magnetically responsive. Other patents which may be considered to be of interest include U.S. Pat. No. 4,152,210 to Robinson et al.; 4,335, 094 to Mosbach; and 4,070,246 to Kennedy et al. While these patents disclose the preparation or use of magnetic-biologic particles, none of these are considered to be similar to those of the present invention.

U.S. Pat. No. 4,454,234 to Czerlinski is directed to magnetically-responsive microparticles suitable for use in preparing selectively reversible suspensions thereof and the method of making such microparticles. The microparticle core comprises a single particle of magnetically-responsive material having a Curie temperature within the range of 5° C.–65° C. The method for preparing these microparticles involves the steps of pulverizing and fractionating magnetic substances, which steps are carried out above the Curie temperature to provide the desired microcores, followed by coating the resulting microcores, also above the Curie temperature. According to the disclosure of the Czerlinski patent, these steps are purposely carried out above the Curie temperature of the magnetically-responsive microparticles to avoid the possibilities of magnetic attraction that occurs between small particles in suspension.

U.S. Pat. No. 4,452,773 to Molday discloses "colloidal" iron oxide particles coated with non-ionic polysaccharide by forming magnetite in 25% (w/w) polysaccharide solutions. Molday further teaches the covalent linking of bioactive molecules to such formed particles by well-known chemical linking technology. U.S. Pat. No. 4,795,698 to Owen et al., which is incorporated by reference herein, teaches the preparation of colloidal sized metal oxide particles which are coated in what is believed to be essentially a covalent manner by polymers or proteins which have substantial numbers of unpaired electrons. Bioactive molecules such as antibodies or enzymes retain biological activity in the Owen et al. process which involves (1) the coprecipitation of transition element oxides and polymer or protein at 0.1 to 1 mg/ml by titration with base to slightly alkaline pH, (2) the subsequent washing of the coprecipitate and (3) the resuspension of the coprecipitate in appropriate buffers followed by mild sonication resulting in colloidal magnetically responsive particles.

A colloidal dispersion of magnetic particles in rocket fuel is disclosed in U.S. Pat. No. 3,215,572 to Papell. The dispersion is said to include magnetic particles, such as magnetite ($Fe_3O_4$), $0.25\mu$ in diameter and smaller, preferably less than $0.10\mu$ in diameter. The dispersion is produced by ball milling a suspension of larger particle size magnetic particles in the propellant, with a grinding agent which prevents "agglomeration or welding of the minute particles as grinding progresses" (column 2, lines 33–34). The ball mill includes metal balls to produce the grinding action. The grinding agent, generally included at levels on the order of 2% but possibly up to 10%, typically comprises oleic acid; it is further disclosed, however, that other grinding agents such as stearic acid and cetyl alcohol may be utilized in the production of a magnetic propellant and other long chain hydrocarbons having similar high surface tensions, such as benzene, ethane, hydrazine and gasoline may be utilized as the particle carrier and major constituent of the magnetic propellant (column 4, lines 5–6).

U.S. application Ser. No. 397,106 discloses a method for producing polymer/protein coated magnetic particles which involves disrupting pre-formed crystal agglomerates (magnetite related transition element oxides) in the presence of coating material to produce materials which are in the 25 nm to micron size range. The size of the resultant product depends on the degree and conditions for disruption and the ratio of coat material to crystal agglomerates. Sonication under various conditions is disclosed as the method of choice. For polymer coated materials this process has major advantage over those where metal oxides are formed in situ in the presence of coat material, such as in Molday or Owen. By separating the process of preparing transition element oxide crystals from the coating step interference of coat material in the former process is avoided. Such interference can result in a variety of disadvantages such as heterogeneous crystal growth, difficulty in controlling the oxide process and imperfections in crystals, all of which can compromise the final product. Application Ser. No. 08/231,379, which is a CIP of U.S. application Ser. No. 397,106 relates to another modification which in many respects constitutes an improvement upon the above described process, wherein crystal agglomerate disruption is performed in the absence of coating material. That modification has advantage when material to be coated is adversely affected by the disruption process. Another advantage of separating the disruption from the coating step is that the presence of coating material can inhibit disruption by linking two crystal agglomerates together thus interfering with the disruption process.

Despite the simplicity of the processes described in the last mentioned patent applications and the utility of the resultant material, materials derived from these processes are limited in certain respects. One limitation of these materials is their loss of stability in moderate (0.01M) ionic strength buffers which causes them to agglomerate and eventually settle from solution. Thus in the manufacturing process variation in ionic strength which leads to agglomeration should be avoided. Further such materials will generally only resuspend after magnetic collection if they are in buffers of low ionic strength. Even then, repeated magnetic collection and resuspension can lead to agglomerates. This property can, however, be advantageous as in the case of doing immunoassays in serum or ionic strength buffers near 0.15M. Since these media lead to some agglomeration during the incubation period of the assay and since agglomerates require smaller magnetic gradients to be pulled from solution, this property which is undesirable in some instances becomes a positive benefit and permits the use of material of smaller size than would be the case in the absence this phenomenon or alternatively allows the use of lower magnetic gradient separation devices.

On the other hand, there are many applications where size integrity of the magnetic colloid is very important and where such agglomeration is highly undesirable. One example would be the use of these materials in laboratory or bioprocessing isolations of monoclonal antibodies (MAbs) from ascites fluid or from culture. Typically such media are at physiological ionic strength (0.15 M) and, for example, when Protein A is used to bind MAbs and subsequently desorb MAbs, buffers of such ionic strength or considerably higher are used. There are also instances in immunoassay where agglomeration is not desirable, such as dual stage incubations. For example, to assay for chronic hepatitis, a typical approach would involve incubating ferrofluid specific for human IgM with patient serum so as to capture the IgM in the sample. Capture would be accomplished by magnetically separating the capture material and subsequently washing out non specific proteins. Next the ferrofluid bearing patient IgM would be incubated with excess labeled hepatitis antigen, separated again, washed and the label detected by some appropriate means. The dual incubations of this process and the two separations require a material that will be stable to both moderate ionic strength and to multiple magnetic separations and resuspensions.

During the course of extensive research and development on the above processes, several observations have led to the speculation that the problem of high ionic strength colloidal instability might be due to incomplete crystal agglomerate coverage by the coat polymer/proteins employed. Further, even though it is very difficult to calculate accurately the surface area of such agglomerates and the amount of coat material which should be adsorbed thereon as a monolayer, calculation does suggest that incomplete coverage is a possibility. From extensive experience with dispersed magnetite crystal agglomerates, it is apparent that surface charge is critical to keeping the agglomerates dispersed. This can be seen by performing a simple experiment such as sonicating magnetite in low ionic strength phosphate buffer (10–20 mM). Such a process will result in a transitionally stable dispersion. If such material, while in the dispersed state, is magnetically collected it will be found to not resuspend. The dispersion can also quickly be agglomerated by merely increasing the ionic strength with simple salts. Further evidence suggesting that this process does not result in complete coating is: (1) anionic polymer, dextran or bovine serum albumin (BSA) coated materials non-specifically stick to mammalian cells, and binding can in part be diminished with anionic polymers which can compete with cell surface sialic acid for "bare spots" which would have positive charge due to iron atoms at the crystal surfaces (see U.S. patent application Ser. No. 07/976,476); (2) a substantial portion of material collected by HGMS using very fine steel wool (gradients in excess of 150 kGauss/cm) aggregates in the process; and (3) the size of materials is affected by ionic strength and at ionic strengths as low as 0.02 M agglomeration can be observed.

It would be desirable to have a well coated particulate base material for several reasons. By coating material to a greater degree with a hydrophilic coating, stability in high ionic strength media should be achievable, covering "bare spots" should reduce non-specific binding to cell surfaces, and better coated material should generally permit greater amounts of bioreceptor to be coupled yielding higher bioactivity. There are also process advantages that should accrue since better coated materials can be magnetically collected and resuspended without fear of crystal—crystal interaction which will lead to aggregation. The independence of such processes from concerns of high ionic strength induced aggregation also would be of significant benefit in various manufacturing steps such as purification. Clearly it is simpler to employ magnetics to remove unbound reagent in some particular step rather than to employ column chromatography.

SUMMARY OF THE INVENTION

This invention relates to the production of magnetically responsive superparamagnetic particles which are colloidally stable in high ionic strength systems, e.g. 1.0 to 2.0 M NaCl, and which can repeatedly be subjected to high gradient magnetic separation and resuspension without growth in size as would be evidenced by the appearance of turbidity or particle size growth. Such materials provide process advantages in manufacture which significantly decrease cost of production. These advantages include the ability to repeatedly separate the resultant particles from reagents via magnetic separation rather than using column chromatography, a significantly greater latitude in choice of buffers (types and buffer strengths) which can be used in these processes and also in coupling chemistries or modification/derivatization reactions. These materials also have a significantly greater ability to be filter sterilized (for materials below 200 nm) as regards the amount of product which passes such filters. Further, they are compatible with a greater choice of filter material. These materials also demonstrate significantly lower nonspecific binding, particularly to mammalian cells. This new class of material also has significant application advantages such as ability to undergo repeated separation and resuspension as is often required for multi-incubation assays. Due to their increased content of coating material, they have a greater ability to couple greater amounts of bioligand to them. In such applications where the presence of these materials quenches or absorbs developed signal, such as in chemiluminescent immunoassays or nucleic acid detection, the higher biological activity results in the ability to use less material, which results in greater signal output. This higher biological activity as well as colloidal stability under a wide range of conditions typically found in biological and bioprocessing systems and likely to be found in various other manufacturing applications or processes gives these materials significant advantage over magnetic-polymer particles made by previously available procedures. These materials indeed represent a significant advance over the prior art for coating clusters of crystals of various transition element oxides, and particularly magnetite.

Magnetic particles of small size (maximum particle size generally below $0.2\mu$) with a stabilizing (preferably biochemically or biologically active) coating, are produced, in accordance with one embodiment of the process of the invention, by forming a suspension of somewhat larger size parent magnetic particles (believed to be agglomerates), together with a material adapted to form a coating on the relatively smaller, subdivided "sub-particles" upon subdivision of the parent particles. This mixture is then treated to subdivide or disrupt the parent particles and to maintain those particles in that state, and subjecting the mixture to appropriate heating to form a coating on the deagglomerated or subdivided particles, thus stabilizing them at reduced particle size. The product is a stable suspension.

With the proper selection of coating material, the coated, subdivided particle product can be separated and resuspended. The resultant resuspendable product, if the stabilizing coating is a bioactive compound or ligand, is particularly useful as an MRI contrast agent, for bioanalytical applications and for industrial bioprocessing.

The magnetic particles of the invention can also be prepared by an alternative direct coating process performed on a transiently stable particulate magnetic substrate, which is further described hereinbelow. In carrying out this embodiment of the invention, a particulate magnetic starting material is divided into a plurality of smaller sized particles with the ability to aggregate, thereby providing a bare or uncoated particulate magnetic substrate. The particulate magnetic substrate thus obtained, which is suspended in a suitable liquid medium, is then contacted with an appropriate coating material to form a mixture, before substantial particulate magnetic substrate aggregation occurs, and the mixture is subjected to appropriate heating for a time sufficient for the coating material to adhere to the substrate particles, thereby yielding the desired resuspendable, coated magnetic particles.

Thus, it is not essential to subdivide the particulate magnetic starting material in the presence of the coating material in order to obtain useful colloidal magnetic particles coated with a biologically active biofunctional ligand, for example. Rather, this latter embodiment enables the coating of pre-formed, transiently stable particulate magnetic substrate. The period of stability of the substrate particles is readily determinable by routine experiment in the manner described below. This approach provides certain notable advantages, among which is avoidance of any deleterious effects that the selected disruption technique may have on the coating material. Moreover, sequential addition of coating materials eliminates certain operational restrictions inherent in the embodiment in which the particulate starting material is subdivided in the presence of the coating material. This may be of some importance where the primary coating material is present in a mixture with other substances having greater affinity for the magnetic particulate substrate. Also, because sequential coating affords greater control of the amount of coating material used, work up of the final product is greatly simplified.

The instant invention is based on the surprising discovery that coating of polymer or protein on to such crystals is markedly affected and enhanced by heat. More specifically if the coating reaction is done at temperatures well above those temperatures at which processes involving proteins normally are done, not only is significantly more coating achieved but a product which is colloidally stable in high ionic strength is obtained. Contrary to the notion that protein coating reactions are best done in the cold or at the highest 37° C., it has been discovered that if magnetite slurries are mixed with protein such as BSA and heated to temperatures higher than 60° C., typically 75 to 80° C., and sonicated, a product results which is salt stable and which can be separated and resuspended repeatedly. It has further been discovered that if the sonication of such mixtures is done in the cold (0 to 5° C.) such as described in U.S. application Ser. No. 397,106, and the mixture subsequently heated to 75° C. while still in the presence of excess coating material, the product obtained will have the same properties as described above. This result demonstrates that the conversion to a salt stable material is independent of the sonication treatment and clearly only depends on the high temperature coating reaction. To examine if the coating reaction can be done in two steps as disclosed in U.S. application Ser. No. 08/231,379 where slurries of magnetite are first sonicated to a dispersion of crystal agglomerates—single crystals up to agglomerates as large as 200 nm, depending on the degree of disruption—and subsequently coated in an independent step, magnetite was dispersed by sonication at 5° C. or at 75° C. and subsequently coated with protein/polymer at 75° C. In both cases product results which is stable to high concentrations of simple salts, 2 M NaCl and to repeated magnetic separation and redispersion.

DETAILED DESCRIPTION OF THE INVENTION

It is hypothesized that magnetic materials, or more generally, transition element oxides, in particle form, tend to have significant surface polarity, which is minimized by agglomeration of crystals of such materials. When these crystal agglomerates are subdivided or disrupted, they tend to become unstable, again forming crystal agglomerates over time. In accordance with the present invention, the nascent (and probably charged) surfaces of these sub-particles are stabilized by the coating material which may be deposited simultaneously or sequentially on these surfaces as the parent particles are sub-divided or thereafter, but before crystal agglomerates begin to form. For that purpose, the coating material may be chosen on the basis of its tendency to respond to the surface polarity of the deagglomerated magnetic particle and various coating materials will thus react differently with different particulate magnetic materials. If the treating or disrupting technique is, or includes, pH modification, the effect of pH modification on sub-particle surface polarity and coating material polarity may also be a consideration. The coating material is selected in each case with regard to its ability to adhere to, or be adsorbed on or otherwise modify a property of the surface of the deagglomerated or sub-divided particle so that the stability of the particle product of reduced size is retained, to provide a stable suspension thereof.

In investigating means for coating disrupted particles where coating is done either simultaneously with disruption or sequentially, it has been discovered that such reactions are markedly enhanced by heating to high temperatures. Temperatures from about 45–50° C. are effective and temperatures as high as 85° C. have been employed with 75° C. appearing to be optimal. In the case of protein coatings and certain polymers which have secondary and tertiary structure, it is surprising that these materials can be treated in this manner. The resultant resuspendable products have the characteristics of showing low nonspecific binding to cells as well as macromoleules, have significantly higher levels of coat material than non heat treated product and most of all have the unusual property that they maintain colloidal stability in high ionic strength buffers. Depending on the degree of heating (temperature or time,) materials which are stable in 0.5 M NaCl up to 2.0 M NaCl can be produced.

Magnetic compounds which may be used as the starting material in the present invention include the transition metal oxides, sulfides, silicides and carbides, optionally having different transition metals in a single magnetic compound, such as $Gd_3Fe_5O_{12}$. Preferred is the class of magnetic oxides known as ferrites, generally represented as $MO \cdot Fe_2O_3$ in which M is Zn, Gd, V, Fe, In, Cu, Co, Mg, and in particular magnetite ($FeO \cdot Fe_2O_3$).

Representative examples of suitable transition metal oxides that are useful in the practice of this invention, and their corresponding Curie temperatures, are as follows:

| Formula | Chemical Name | Curie Temp (° C.) |
| --- | --- | --- |
| $CrO_2$ | chromium (IV) oxide | 117 |
| $COFe_2O_4$ | cobalt ferrite | 520 |
| $CuFe_2O_4$ | copper ferrite | 505 |
| $Dy_3Fe_5O_{12}$ | dysprosium ferrogarnet | 237 |
| $DyFeO_3$ | dysprosium orthoferrite | 270 |
| $ErFeO_3$ | erbium orthoferrite | 260 |
| $Fe_5Gd_3O_{12}$ | gadolinium ferrogarnet | 202 |
| $Fe_5HO_3O_{12}$ | holmium iron garnet | 217 |
| $FeMnNiO_4$ | iron nickel manganese oxide | 287 |
| $Fe_2O_3$ | γ-iron oxide (maghemite) | 670 |
| $Fe_3O_4$ | iron (II,III) oxide (magnetite) | 602 |
| $Fe_2O_3$ | α-iron oxide (hematite) | 685 |
| $FeLaO_3$ | lanthanum ferrite | 465 |
| $MgFe_2O_4$ | magnesium ferrite | 310 |
| $Fe_2MnO_4$ | manganese ferrite | 286 |
| $MnO_2$ | manganese dioxide | 777 |
| $Nd_2O_7Ti_2$ | neodymium dititanate | 1885 |
| $Al_{0.2}Fe_{1.8}NiO_4$ | aluminum nickel ferrite | 473 |
| $Fe_2Ni_{0.5}O_4Zn_{0.5}$ | nickel-zinc ferrite | 272 |
| $Fe_2Ni_{0.4}O_4Zn_{0.6}$ | nickel zinc ferrite | 280 |
| $Fe_2Ni_{0.8}O_4Zn_{0.2}$ | nickel zinc ferrite | 479 |
| $NiO$ | nickel (II) oxide | 350 |
| $Fe_2NiO_4$ | nickel ferrite | 595 |
| $Fe_5O_{12}Sm_3$ | sarnarium ferrogarnet | 310 |
| $Ag_{0.5}Fe_{12}La_{0.5}O_{19}$ | silver lanthan ferrite | 430 |
| $Fe_5O_{12}Y_3$ | yttrium iron garnet | 257 |
| $FeO_3Y$ | yttrium orthoferrite | 375 |

In addition to the transition element-containing compounds described by Owen et al. and the ferrites noted above, a class of magnetic metal oxide which does not contain iron can be coated as described in this invention. These compounds include oxides of combinations of two or more of the following metal ions: Al(+3), Ti(+4), V(+3), Mn(+2), Co(+2), Ni(+2), Mo(+5), Pd(+3), Ag(+1), Cd(+2), Gd(+3), Tb(+3), Dy(+3), Er(+3), Tm(+3) and Hg(+1). They differ from ferrites in both appearance and magnetic susceptibility. The non-ferrites can take any color from white or yellow to green and even brown. This makes them particularly useful in spectrophotometric applications. Non-ferrites are generally less strongly magnetic than ferrites and, as such, pass through HGMS filters in magnetic fields capable of collecting ferrite based materials which permits selective magnetic retrieval.

The non-ferrous oxides can be employed in place of the metal oxides described by Whitehead et al. to produce silane coated magnetic particles which have the desirable properties given above. Similarly, when the chlorides (or sulfates) of such combinations are employed according to the methods taught by Molday or by Owen et al., coated product having very desirable magnetic and spectral properties can be obtained.

Coating materials which may be used are preferably in aqueous suspension or solution, although suitable coating materials in non-aqueous liquid media or in the form of melts may also be used. The coating material is usually a synthetic or natural polymer and may be a protein, a peptide or a nucleic acid. In principle, however, the coating material can be any substance which has affinity for the surfaces of such crystals and which is not adversely affected by these high temperatures.

In carrying out the process of the invention involving disruption of the particulate magnetic starting material in the presence of the coating material, the two materials are combined in a liquid mixture, usually including a third liquid component, such as water, to form a suspension. The relative proportions of these materials in this mixture is not believed to be critical. However, in general, the proportion of magnetic particles to coating material is from 1000:1 to 1:10 (by weight).

To make stable suspensions of coated sub-particles of the magnetic starting material, the mixture may be treated in a number of ways to disrupt or sub-divide the magnetic particulate starting material. These include mechanical and chemical means, such as mild heat, vibration, irradiation, sonication, pH modification, or a combination of these. Of these, sonication is particularly preferred. During or following this process the system is heated, preferably to 75° C. and maintained at that temperature until coating is maximized.

Alternatively, sub-division of the magnetic particulate starting material can be done in the absence of coating material, followed by a subsequent heat driven coating step. This can be accomplished at temperatures ranging from 0° C. up to 85° C. and as above, various mechanical or chemical means can be employed. A preferred embodiment for the disruption of magnetic particulate material has been found to be disruption at 0 to 5° C. in the presence of low concentrations of neutral phosphate buffer (5 to 30 mM) and employing sonication as the means for disruption. Keeping the temperature in this range seems to confer two advantages over higher temperature disruption which are oxidation and subsequent magnetic compromise of the crystals is avoided at the lower temperatures and secondly that smaller crystal agglomerates can be obtained for the same energy input. By disrupting magnetic material in the absence of coating material, a distribution of crystal agglomerate sizes is produced, which are resuspendable. The mean of the distribution has been found to be related to energy input (time and power of sonication), to the presence of various chemical species before and/or during the disruption process, the magnetic saturation value of the material and the manner in which the crystals are prepared. For example, in the preparation of magnetite and other transition metal oxides, the rate of addition of base (or the nature of the base, e.g., $NH_4OH$ vs NaOH) in forming the oxides from the chloride or sulfate salts results in crystals which vary in size and which can be disrupted to different degrees. For example, fast addition of NaOH to the sulfate salts of iron results in magnetite crystal clusters which typically are smaller than those formed either by slow addition or by employing $NH_4OH$ to effect the oxidation. Once the distribution of crystal agglomerates is formed, coating material is rapidly mixed in at a concentration sufficient to arrest reagglomeration and the mixture is heated to drive the coating reaction. The coating material can be at the same temperature or at some higher temperature. According to a particularly preferred embodiment, the magnetic starting material is subdivided, with heating, in the absence of the coating material, and subsequently mixed with coating material at 75–80° C., with continued heating at 75° C. for 30 to 40 minutes.

As those skilled in the art will realize there are several advantages to separating the disruption step from the step which prevents reagglomeration from the step which drives and completes the coating. Clearly if the disruption step is done at high temperature in the presence of coating material where the coating reaction clearly is more avid, then the presence of coat material should likely interfere with the disruption reaction. Even though high ionic strength colloidally stable material can be produced in this manner, the fact that so many and varied reactions are occurring at the higher temperature suggests that such a process would be difficult to control. On the other hand, performing the disruption reaction in the absence of coat material in principle should be a controllable process, given that one starts each preparative procedure with material which at the crystal level is very similar in size, structure and in the case of magnetic materials, of similar magnetic character. By arresting the disrupted system from reagglomeration by adding coating material in a sufficient quantity to prevent reagglomeration and then heating the system to drive the coat reaction, one minimizes the possibility that coat material will crosslink near neighbor crystal agglomerates.

Although the foregoing methods of the invention have been characterized as coating methods, such methods may aptly be considered extraction methods, depending on the particular application. Thus, the methods described herein may be beneficially utilized for the specific purpose of extraction of a target material from a complex mixture, such as isolation of environmentally hazardous materials from a waste stream, product recovery from a reaction mixture or the separation of a component of value from a mixture comprising generally worthless components.

In carrying out this process, the particulate magnetic starting material may be disrupted to form a transient colloid, as described herein, to which a test sample containing the target molecule to be bound is subsequently added, or the particulate magnetic starting material can be disrupted in the presence of the target molecule.

The examples set forth below demonstrate that treatment of subdivided magnetic particulates with various chemical agents, such as acid or base, for adjustment of pH (or ionic strength), markedly affects binding selectivity for various polyanions and polycations. Thus, it is clear that as a means for performing extraction, this procedure offers considerable specificity for the polyelectrolyte of interest. By adjusting solvent, buffer and salt conditions after the binding step and after the bound polyelectrolyte material has been magnetically separated, the target polyelectrolyte is readily recoverable in biologically active form. After recovery of the target polyelectrolyte, the particulate magnetic material may be recycled.

It should be appreciated that this process will function even with transition element oxides materials which have relatively low magnetic susceptibility properties as described hereinabove. In those cases where the material used for polyelectrolyte capture is not sufficiently magnetic for magnetic separation to be effective, filtration could be used for separation and subsequent recovery.

The following examples will serve to illustrate the principles of this invention; however, these examples should not be construed as limiting the scope of this invention.

EXAMPLE 1

Hot Sonicated Magnetite Followed by Hot Coating Reaction

All reagents and chemicals used in these experiments were of analytical grade and obtained from Fisher Scientific (Pittsburgh, Pa.) unless otherwise specified. Magnetite was prepared by mixing solutions of 17 g and 12 g of ferric sulfate pentahydrate and ferrous sulfate heptahydrate, respectively, in water with stirring at 70° C. under a nitrogen atmosphere while raising the pH with 60 ml of ammonium hydroxide. The resultant magnetite was collected magnetically, washed 10 times with distilled water and resuspended in 600 ml distilled water. The preparation so made contained approx. 10 mg/ml magnetite.

To make bovine serum albumin (BSA)-ferrofluid, 1.0 gram of the magnetite prepared above was measured into a beaker and magnetically washed with water two times. The final resuspension was into 100 ml of 20 mM sodium phosphate, pH 7.5. The magnetite was preheated to 70° C., then sonicated with a Fisher Sonic Dismembrator Model 550 for 20 minutes with pulse sonication 1 second on/1 second off (total time 40 min.) at a power setting of 7. Meanwhile, 1.8 g of BSA was dissolved in 60 ml of 20 mM sodium phosphate, pH 7.5, and heated for 10 min. at 75° C. After sonication, 30 ml of the sonicated magnetite was quickly removed, mixed with the hot BSA and heated for 5–20 minutes at 75° C., then cooled in an ice bath. The ferrofluid size distribution was narrowed by a series of controlled magnetic washes in a chamber having a 3 kGauss field at its surface. Material collected in a fixed time interval was retained. Routinely, this procedure was done three times for each preparation. Hereinafter this process is referred to as high field washes. Values for size, salt stability, and adsorbed protein as measured by carbon analysis are tabulated in Table I, rows 1–3.

EXAMPLE 2

Cold Sonicated Magnetite Followed by Hot Coating Reaction

Magnetite was prepared as described in example 1 above. To make BSA ferrofluid, 3.6 grams of BSA was dissolved in 120 ml of 20 mM sodium phosphate, pH 7.5, and heated for 10 min. at 75° C. Meanwhile, 1.0 gram of the magnetite prepared above was measured into a beaker and magnetically washed with water two times. The final resuspension was into 100 ml of 20 mM sodium phosphate, pH 7.5. The magnetite was sonicated with a Fisher Sonic Dismembrator Model 550 for 30 minutes at 10° C. with pulse sonication 1 second on/1 second off (total time 60 min.) at a power setting of 7. The sonication temperature was controlled with a circulating cooling system containing ethylene glycol at −4° C. After sonication, 60 ml of the sonicated magnetite was quickly removed and mixed with the hot BSA and heated for 5–60 minutes at 75° C., then cooled in an ice bath. The ferrofluid was washed in the high field. Measurements of size, salt stability, and adsorbed carbon are tabulated in Table I, rows 4–9.

EXAMPLE 3

Measurement of Salt Stability and Adsorbed Protein of Ferrofluid

To measure the salt stability of the preparation of BSA ferrofluid, 0.25 ml samples of the ferrofluid were placed in NaCl-containing phosphate buffer such that the final concentrations were 0, 0.5, 1.0, and sometimes 2.0 M in sodium chloride. The samples were then sized with a Coulter N4CD Submicron Particle Analyzer (Coulter Corp., Hialeah, Fla.) at t=0, 1, 2, 4, and 17 hours at room temperature.

To measure the amount of adsorbed protein, 2–3 mg of ferrofluid was mixed with 1 ml concentrated HCl, placed in a glass ampoule, and sealed. After overnight digestion at 110° C., the sample was neutralized to a pH of 2–4. The total adsorbed carbon was measured with a TOC 5000 (Shimadzu, Kyoto, Japan.) The results of the above procedure are summarized for the ferrofluids prepared in examples 1 & 2 in Table I, below. As a control, one sample of ferrofluid (cold sonicated magnetite as described in example 2) was mixed with the BSA and left unheated at room temperature (20° C.) for 30 minutes, see row 10.

TABLE 1

| Row | Sonication conditions | Post heat time with BSA | Size (nm) | Salt stability: followed by change in size (nm) after 17 hours @ RT. | | | TOC (µg BSA/ mgFe) |
| --- | --- | --- | --- | --- | --- | --- | --- |
| | | | | 0 M | 0.5 M | 1.0 M | |
| 1 | Sonicating BM alone, hot for 20 min followed by post heating with BSA. | 5 min. | 146 | 144 | 170 | 500 | 255 |
| 2 | | 10 min | 139 | 144 | 148 | 194 | 324.1 |
| 3 | | 20 min | 144 | 148 | 148 | 153 | 351 |
| 4 | Sonicating BM alone, cold for 30 min followed by post heating with BSA. | 5 min. | 145 | 157 | 683 | 1985 | 278 |
| 5 | | 10 min | 145 | 154 | 350 | 982 | n.d. |
| 6 | | 20 min | 144 | 155 | 151 | 265 | n.d. |
| 7 | | 30 min | 145 | 159 | 169 | 337 | n.d. |
| 8 | | 45 min | 149 | 156 | 157 | 188 | 343 |
| 9 | | 60 min | 154 | 165 | 173 | 185 | 359 |
| 10 | Sonicating BM alone, cold for 30 min followed by cold incubation with BSA. | Cold 30 min | 266 | 862 | 1675 | 1510 | 134 | n.d. = not determined
BM = bare (uncoated) magnetite slurries

The margin of error in the size data is approximately 5%, so small changes are within error. However, larger sized changes are significant. A particle above approx. 300 nm will eventually irreversibly settle out of solution. The margin of error in the adsorbed carbon data is approximately 4%. Note that the longer "post heat time" with the BSA results in ferrofluid that are highly coated (>300 ug BSA/mg Fe) with BSA. Also note that the size of these ferrofluid particles remains relatively constant, even at high salt concentration, which satisfies the criteria for salt stability. Finally note that cold control (row 10) has significantly less of a BSA coating, and it is highly unstable in even salt solutions containing only buffer ions (20 mM phosphate).

EXAMPLE 4

Heat Treatment of Cold Sonicated BSA Ferrofluid

Ferrofluid can be prepared as disclosed in U.S. patent application Ser. No. 397,106, with a cold sonication of a mixture of magnetite and protein. The heating of this ferrofluid will also result in increased protein coating and salt stability. Magnetite was prepared as described in example 1, above. BSA ferrofluid was prepared by mixing 2.0 g of BSA with 1.0 g of magnetite in 200 ml. Then the mixture was sonicated with a Fisher Sonic Dismembrator Model 550 for 45 minutes with pulse sonication 1 second on/1 second off (total time 90 min.) at a power setting of 7. The sonication temperature was controlled with a circulating cooling system containing ethylene glycol at $-4°$ C. The measured temperature during the sonication was $30°$ C. Then the resultant ferrofluid was heated for varying times ranging from 0–90 minutes at $80°$ C.

The adsorbed protein was measured by the protein assay kit commercially available from the BioRad Corp. (Richmond, Calif.) The samples were prepared for the assay by removing all magnetic particles from solution with a 5 min HGMS pull in a microtiter well fitted with a wire screen placed in an Immunicon Protein Separator as described in U.S. Pat. No. 5,200,084 (Immunicon Corp., Huntingdon Valley, Pa.). The supernatant was removed from the microtiter well with a pipet, diluted, and the assay was performed as directed in the kit's instructions, using a standard curve prepared from pure BSA. The protein bound to the magnetic particle was determined by subtraction of the amount of BSA found in the non-magnetic supernatant from the original amount of BSA added to the magnetite.

The initial amount of protein adsorbed was 0.05 mg BSA per mg of iron. The amount adsorbed remained reasonably steady over the first thirty minutes of the experiment, within the range of 0.10 to 0.15 mg of BSA adsorbed. A sudden increase in the amount of protein adsorbed was detected at approximately 30 minutes which correlates with an increase in the salt stability (data not shown). Measurements of protein adsorption were continued periodically over the next hour, and were found to be in the range of 0.30 to 0.35 mg BSA per mg iron, with a majority of the measurements being at or about the latter value.

EXAMPLE 5

Non-specific Binding as a Function of Heating During Sonication Time

Magnetite was prepared as in example 1 above. To make BSA ferrofluid, 0.175 gram of the magnetite was measured into a beaker and magnetically washed with water two times. The final resuspension was into 35 ml of BSA solution prepared at 10 mg/ml in 10 mM sodium phosphate, pH 7.5. The mixture was placed in a jacketed beaker (Heat Systems, Farmingdale, N.Y.) and cooled or warmed to temperatures listed in Table II below. Then the mixture was sonicated with a Fisher Sonic Dismembrator for 20 minutes with pulse sonication 1 second on/1 second off (total time 40 min.) at a power setting of 7. The actual temperature of the sonicate was measured. After sonication, the BioRad Assay was performed as described in example 4 to determine the amount of bound protein. Then the ferrofluid size distribution was narrowed by a series of 3 magnetic washes with "high field magnets." Resuspension was into 10 mM sodium phosphate, pH 7.5. Then the ferrofluid was further fractionated with two "low field" magnetic washes. The strength of the magnetic field was approximately 0.4 kGauss at the collection surface. In this case, only the supernatant was collected after each wash, and the pellet was discarded.

Size, salt stability, and intrinsic NSB were measured at this point. NSB (non-specific binding) is defined in this case as the percentage of cells removed from solution when the cells are mixed with a ferrofluid, which is then allowed to magnetically collect. In the ferrofluid/cell solution, there is no substance that should cause the ferrofluid and cells to interact. For example, no antibodies, lectins, or common capture agents, such as biotin, streptavidin, haptens, or Protein A or G are present. The NSB was measured with a radioactive difference assay. CEM cells were labeled with $^{51}$Cr by suspending up to $5.0 \times 10^7$ cells in 2 ml of RPMI supplemented with 10% fetal calf serum, 100 units of penicillin-streptomycin, and 1.25% L-glutamine (all supplied by Mediatech, Washington, D.C.). $^{51}$Cr was obtained from Dupont (Wilmington, Del.) and used straight from the bottle. The cpm of the chromium was determined by counting in a Cobra II Gamma Counter (Packard, Downer's Grove, Ill.). Approximately $1 \times 10^7$ cpm's were added to the cells and incubated at $37°$ C. for 1 hour, vortexing every 15 minutes. For the assay, 160 $\mu$l of labeled cells at $2.5 \times 10^6$ cells/ml were mixed with 160 $\mu$l of ferrofluid at 20 $\mu$g Fe/ml in isotonic phosphate buffered saline (IPBS) in a test tube. The mixture was incubated for 5 minutes. During the incubation time, the counts of $^{51}$Cr were determined by counting in the gamma counter. Then 250 $\mu$l of the mixture was placed into a microtiter well, and the ferrofluid was removed with a 5 minute magnetic depletion in an Immunicon Cell Separator as described in U.S. Pat. No. 5,200,084 (Immunicon Corp., Huntingdon Valley, Pa.). After depletion, the microtiter well(s) were removed and individually placed into test tubes. The number of counts were recorded. Additionally, the incubation mixture remaining in the test tube after the sample was removed to the microtiter well was counted for $^{51}$Cr. The starting number of counts was determined by subtracting these counts remaining in the test tube from the number of counts initially added to each test tube. Percentage removal (NSB) was determined by the following equation:

$$NSB = \frac{(100\%)(\text{starting counts} - \text{counts in microtiter well})}{(\text{starting counts})}$$

Data for this example are tabulated in Table II below. Note that only above approximately $60°$ C. actual sonication temperature does the ferrofluid become salt stable. At the higher temperatures, the NSB drops as well, which could be caused by the elimination of "bare spots" on the magnetic particle, which due to the positive charge of the iron, may tend to inherently bind to cells, non-specifically removing them from solution.

TABLE II

| Temp (° C.) | Actual Sonication Temp (° C.) | Adsorbed Protein (μg BSA/mgFe) | Salt stability: followed by change in size (nm) in 0.75 M NaCl | | | NSB (%) |
|---|---|---|---|---|---|---|
| | | | 0 hr | 2 hr | 25 hr | |
| −4 | 31 | 73.4 | 91 | settled | settled | 90.7 |
| 10 | 38 | 117 | 93 | settled | settled | 87.7 |
| 25 | 47 | n.d. | 103 | 755 | settled | 55 3 |
| 35 | 55 | n.d. | 107 | 144 | settled | 39.6 |
| 45 | 62 | 196 | 113 | 123 | 194 | 38.7 |
| 55 | 69 | 198 | 119 | 123 | 135 | 25.0 |
| 65 | 75 | n.d. | 126 | 130 | 137 | 19.4 |

EXAMPLE 6

Coupling Streptavidin to BSA Ferrofluid

Streptavidin can be coupled to BSA ferrofluid by the following procedure. Hot coated ferrofluid was prepared as in Example 2, with a 60 minute BSA coat-time. The ferrofluid was decanted and washed three times with a high field magnet. After each wash, the ferrofluid was resuspended in 180 ml 0.1 M sodium phosphate, pH 7.5. The BSA ferrofluid was activated using N-succinimidyl-4-(N-maleimido methyl) cylcohexane-1-carboxylate (SMCC) (Pierce, Rockford, Ill.) following the manufacturer's instructions. Then the activated ferrofluid was washed three times. After each wash, the ferrofluid was resuspended in 180 ml 0.1 M sodium phosphate, pH 6.5 at 4° C. An amount of streptavidin (Prozyme, Richmond, Calif.) equal to twice the mass of iron was weighed out and dissolved in 0.1 M sodium phosphate, pH 7.5 with 5 mM EDTA. The streptavidin was activated with Trauts reagent (Pierce, Rockford, Ill.) following the manufacturer's instructions. Then the activated streptavidin was purified over a PD-10 column (Pharmacia Biotech, Uppsala, Sweden) and 1 ml column fractions were collected. Fractions 4 and 5 contained protein and were pooled. The activated ferrofluid and 1.5 mg of activated streptavidin per milligram of iron were then mixed and allowed to react at room temperature for 4 hours with stirring. Then the reaction was quenched with 4 mg/ml mercaptosuccinic acid in 0.1 M sodium phosphate, pH 7.5 with 5 mM EDTA. The quenching reaction was allowed to react at 4° C. for 16 hours with stirring. After the quench reaction, the ferrofluid was washed two times with a high field magnet. After each wash, the ferrofluid was resuspended in 150 ml 0.1 M sodium phosphate, pH 7.5 with 0.2 mg/ml BSA. However, the final resuspension was in 10 mM HEPES, pH 7.5 with 10 mg/ml BSA. The resultant ferrofluid was immersed in a Fisher bath sonicator FS-14 for 2 minutes, then washed into 10 mM HEPES, pH 7.5 with 0.1 mg/ml BSA. A final 0.2 micron filtration was performed.

EXAMPLE 7

Depletion of CEM Cells with Hot Coated Streptavidin Ferrofluid

First anti-CD45 (Becton-Dickinson, San Jose, Calif.) monoclonal was biotinylated through available free amino groups. Approximately 1–2 mg of antibody was prepared in approximately 0.5 ml of 0.05 M sodium bicarbonate, pH 8.5. N-succinimidyl 6-(biotinamido) hexanoate ester (Molecular Probes, Eugene, Oreg.) was dissolved in DMSO and added to the anti-CD45 in excess. The mixture was allowed to react for 2 hours at 4° C. The antibody was purified over a PD-10 column (Pharmacia Biotech, Uppsala, Sweden), taking fractions 3 and 4 (1 ml fractions.)

CEM cells were harvested and suspended in isotonic phosphate buffered saline solution with 1% BSA (1% BSA/IPBS) to a concentration of approximately $2.2 \times 10^7$ cells/ml. A series of 0.85 ml samples of cell suspension were incubated for 10 minutes at room temperature with 1 ug biotinylated anti-CD45. Solutions of streptavidin ferrofluid prepared as in example 6 (lot 188-143-6) and as generally described in U.S. patent application Ser. No. 397,106 (lot 0994-1284W) were then added to the cells in a volume of 0.85 ml. The amount of ferrofluid varied from 12.5 ug to 100 ug of iron. The mixtures were allowed to incubate for 5 minutes at room temperature. Then each sample was pipetted into a 2 ml cell separation chamber as described in U.S. Pat. No. 5,200,084 (Immunicon Corp., Huntingdon Valley, Pa.). The samples were allowed to magnetically collect for 7 minutes, then they were removed from the magnetic field. Each sample was then mixed with a pipet and placed again in the magnetic field for another 7 minute magnetic collection, using a fresh set of pins. Efficacy of depletion was determined by counting cell number with a hemacytometer (Hausser Scientific, Horsham, Pa.) using an ethidium bromide/acridine orange dye, prepared as directed in the BD monoclonal antibody sourcebook and mixed 1:1 with the cell suspension. Results of the depletions are tabulated in Table III below. Note that although both ferrofluids removed the cells efficiently, the hot coated streptavidin ferrofluid removed over 99% of the cells, even at an iron level half of that required by the non-heat treated ferrofluid.

TABLE III

| | Depletion of CEM cells (%) | |
|---|---|---|
| Total Fe/test | FF lot 188-143-6 | FF lot # 0994-1282W |
| 12.5 ug Fe | 99.4% | 88.5% |
| 25.0 ug Fe | 99.3% | 98.9% |
| 50.0 ug Fe | 99.5% | 99.3% |
| 75.0 ug Fe | 99.8% | 99.4% |
| 100.0 ug Fe | 99.3% | 99.5% |

EXAMPLE 8

Comparison of a Hot Coated Ferrofluid with a Non-Heat Treated Ferrofluid

A hot coated ferrofluid was prepared as described in example 2 and coated with streptavidin as described in example 6 (lot #188-191-15). A non-heat-treated streptavidin ferrofluid was prepared similarly to the ferrofluid used in example 7 (lot #0395-1308). As measured by the TOC 5000, the total adsorbed carbon was 278 μg/mg Fe for the hot coated ferrofluid. For a non-heat-treated ferrofluid, the total adsorbed carbon is approx. 145. These measurements were taken on the BSA particle, before any streptavidin coupling. Additionally the hot coated ferrofluid was salt stable, while the non-heat-treated ferrofluid was not.

However, the difference in protein coating and intrinsic behavior continues after the BSA particle is coated with a secondary protein, such as streptavidin. For example, the binding capacity measures the amount of biotinylated protein that can be bound to a streptavidin ferrofluid. The value for binding capacity is closely related to protein coating, as the more streptavidin coats a particle, the more biotinylated BSA (bBSA) it can bind. The assay for binding capacity began with the labeling of biotin BSA with $^{125}$I. Biotin-BSA was biotinylated with N-succinimidyl 6-(biotinamido) hexanoate ester (Molecular Probes, Eugene, Oreg.) following the manufacturer's suggested protocol. It was then purified by running it over a PD-10 column, and diluted to 5 mg/ml with 0.25 M sodium phosphate buffer, pH 7.5. 200 μl of Iodogen (Sigma, St. Louis, Mo.) was placed in a test tube and dried by blowing nitrogen gas over it. One millicurie of $^{125}$I was added to the test tube, followed by 200 μl of the biotin-BSA. The mixture was incubated on ice for 10 minutes. Then 800 μl of the phosphate buffer was added to the tube and the entire volume was loaded onto a fresh PD-10 column. Labeled biotin-BSA was eluted in the fourth and fifth one ml fraction.

The binding capacity assay was begun with preparation of the standards. Standards between 15 and 500 μg bBSA/ml were prepared with 2.5% $^{125}$I labeled biotinylated BSA in a phosphate buffer (20 mM phosphate buffer, pH 7.5, containing 10 mg/ml BSA and 0.15 M NaCl). The ferrofluid was diluted to 400 μg/ml with 20 mM HEPES with 0.1 mg/ml BSA and 0.05% ProClin 300 (Supelco, Inc., Bellefonte, Pa.), pH 7.5. Then the ferrofluid was further diluted ten-fold with the proprietary phosphate buffer noted above and incubated 15 minutes. 100 μl of ferrofluid was placed in each well of a strip of microtiter wells. 100 μl of each standard was then added to each well and allowed to incubate 10 minutes. Then each well was placed in a quadrupole magnetic separator, as described in U.S. Pat. No. 5,186,827, with an opening exactly the size of the microtiter well. After 5 minutes, the non-magnetic supernatant was discarded from each well and the magnetic material was washed five times using PBS buffer with 0.1% Tween 20 with a final resuspension in 20 mM HEPES with 1 mg/ml BSA and 0.05% ProClin 300. Then the wells were removed from the magnetic separator and each well was placed in a 12×75 mm test tube. The cpm remaining in each microtiter well were counted with a gamma counter. Additionally, 10 ul of the 500 μg/ml standard (or 5 ug bBSA) was counted in the gamma counter. This number was multiplied by 0.08 to normalize to 4 μg of bBSA. All sample counts were then divided by this factor and multiplied by 1000 to calculate the number of micrograms of biotin BSA bound per milligram of iron. Results of this binding capacity assay are tabulated in Table IV below for the hot coated ferrofluid (lot#188-191-15) and the non-heat-treated ferrofluid (lot# 0395-1308.) The data indicate that for almost the entire range of bBSA, the ferrofluid manufactured through the hot coated process had approximately twice the binding capacity of a ferrofluid that had not been heat-treated. That is, significantly more biotinylated protein could be bound by the ferrofluid, once the particle had been coated with streptavidin.

TABLE IV

| | ug bBSA/mg Fe | |
|---|---|---|
| ug bBSA/test | FF lot 188-191-15 | FF lot 0395-1308 |
| 0 | 0 | 0 |
| 1.56 | | 29 |
| 3.13 | 67 | 43 |
| 6.25 | 91 | 53 |
| 12.5 | 96 | 62 |
| 25.0 | 121 | 70 |
| 37.5 | 131 | 71 |
| 50.0 | 120 | 64 |

Another result of the amount of streptavidin bound to a ferrofluid particle is the performance of the ferrofluid in removing cells labeled with biotinylated antibody from solution. Particles with more streptavidin bound can remove more cells at lower amounts of iron. An assay for performance uses non-radioactive CEM cells at $1.0 \times 10^7$ cells/ml. 2 ml of cells were mixed with 2.0 μg of biotinylated anti-CD45, prepared as described in example 7. The cells and antibody were incubated for 30 minutes. Then 150 μl of the cell mixture was placed into each of a strip of microtiter wells and then mixed with 150 μl of ferrofluid at 1.5–25 μg/ml. The ferrofluid had been pre-incubated with a blocking buffer (Ferrofluid Dilution Buffer, available from Immunicon Corporation, Huntingdon Valley, Pa.) for at least 30 minutes. A ten minute incubation was followed by a 5 minute separation in the Immunicon Cell Separator as described in example 7. After removal from the Cell Separator, the supernatant in the wells was mixed with a pipet and 100 μl of sample were removed to a cell counting vial filled with 10 ml of Isotonic Hematall Diluent. The cell numbers were measured with a Coulter ZF Cell Counter (Coulter, Hialeah, Fla.). Depletion was measured by percentage of cells removed from the sample compared to a sample which had buffer added in place of ferrofluid. Depletions at various iron concentrations are tabulated in Table V below. It should be noted that although at high iron values, both ferrofluids deplete similar percentages of cells, at the lower iron values, the hot coated ferrofluid removes significantly more cells.

TABLE V

| | Assay for Performance with CEM cells (% removal) | |
|---|---|---|
| [Fe] ug/ml (final) | FF lot 188-191-15 | FF lot 0395-1308 |
| 0.00 | 0.0 | 0.0 |
| 0.78 | 4.0 | 6.3 |
| 1.56 | 18.3 | 17.1 |
| 3.13 | 71.2 | 47.3 |
| 6.25 | 96.9 | 90.1 |
| 12.5 | 98.7 | 98.1 |

EXAMPLE 9

Depletion of Low Density Fraction Mononuclear Cells with Hot Coated Ferrofluid

Mononuclear cells were isolated from a sample of peripheral blood by density centrifugation with Ficoll-Paque ET (Pharmacia Biotech, Uppsala, Sweden), washed twice in 1%

BSA/IPBS and suspended in the same buffer to a concentration of approximately 26.5×10⁶ cells/ml. Two samples of 0.85 ml each of cell suspension were incubated for 10 minutes at room temperature with 1 ug biotinylated anti-CD45, prepared as in example 7 above. Solutions of streptavidin ferrofluid prepared as in example 6 (lot 188-143-6) were then added to the cells in a volume of 0.85 ml. 10.0 ug and 75 ug of iron/test were used in this experiment. The mixtures were allowed to incubate for 5 minutes at room temperature. Then each sample was pipetted into a 2 ml cell separation chamber as used in example 7 above (Immunicon Corp., Huntingdon Valley, Pa.). The samples were allowed to magnetically collect as in example 7 for two 7 minute magnetic collections with a pipet resuspension between collections. Efficacy of depletion was determined to be 97.2% with 10.0 ug iron and 97.9% with 75.0 ug of iron.

EXAMPLE 10

Coupling Protein A to BSA Ferrofluid

Other proteins can be coupled to the BSA ferrofluids described above. One example is Protein A. BSA ferrofluid was prepared as in example 1 above, except that the total sonication time was 30 minutes. The hot coating was with 600 mg of BSA in 200 ml. After hot coating, the sample was cooled and sonicated for an additional 5 minutes, while cooled in a −4° C. ethylene glycol bath. After an overnight incubation of the ferrofluid at 4° C., the ferrofluid was decanted, fractionated with the high field magnet and washed 4 times with 20 mM HEPES, pH 7.5.

BSA ferrofluid was prepared and activated with SMCC as described in Example 6 above. Protein A (Pharmacia Biotech, Uppsala, Sweden) was activated with a Traut's reagent as described in Example 6. Then 1.0 mg ferrofluid and 1.0 mg Protein A were mixed and incubated one hour at room temperature, then overnight at 4° C. The reaction was quenched with mercaptosuccinic acid as described in Example 6, and the ferrofluid was washed 4 times. Binding capacity of this hot coated Protein A ferrofluid was two times higher than the binding capacity of non-heat treated ferrofluid, otherwise prepared identically, and the material was readily filter sterilizable.

EXAMPLE 11

Coupling Goat Anti-Mouse to BSA Ferrofluid

Goat anti-mouse antibody can also be coupled to BSA ferrofluid. BSA ferrofluid was prepared and activated with SMCC as described in example 10 above. Goat anti-mouse antibody (Jackson Labs, West Grove, Pa.) was activated with a Traut's reagent as described in example 10. Then 30.5 mg ferrofluid and 15.6 mg goat anti-mouse antibody were mixed and incubated one hour at room temperature, then overnight at 4° C. The reaction was quenched with mercaptosuccinic acid as described in Example 10, and the ferrofluid was washed 4 times. Ferrofluid prepared in this manner depleted cells more effectively at low ferrofluid concentrations compared to similarly prepared non-heat treated ferrofluids.

EXAMPLE 12

Preparation of Hot Coated Ferrofluids Using Polymers Other than BSA

It is also possible to prepare heat-treated ferrofluids with polymers and proteins other than BSA. Polymers such as Dextrans T-10 and T-40 (Pharmacia Biotech, Uppsala, Sweden), and proteins such as beta-lactoglobulin (Sigma, St. Louis, Mo.) were used in the process described in example 2, except that the hot coating with the BSA was replaced by a hot coating with the above polymers. Ferrofluids prepared by this hot coating process were compared to ferrofluid prepared by an identical process, but without a heating step and compared by size and total adsorbed carbon. In all cases, the hot coated process resulted in small ferrofluids with a relatively high degree of coating, while the cold process resulted in large, unstable particles, which rapidly settled from solution and had significantly less adsorbed coating material.

While certain preferred embodiments of the present invention have been described and exemplified above, it is not intended to limit the invention to such embodiments, but various modifications may be made thereto, without departing from the scope and spirit of the present invention as set forth in the following claims.

What is claimed is:

1. In a process for making resuspendable, coated magnetic particles by direct application of a coating material to a particulate magnetic substrate, wherein said substrate is prepared from a particulate, magnetic, transition metal oxide starting material selected from the group consisting of chromium (IV) oxide ($CrO_2$), cobalt ferrite ($CoFe_2O_4$), copper ferrite ($CuFe_2O_4$), dysprosium ferrogarnet ($DyFe_5O_{12}$), dysprosium orthoferrite ($DyFeO_3$), erbium orthoferrite ($ErFeO_3$), gadolinium ferrogarnet ($Fe_5Gd_3O_{12}$), holmium iron garnet ($Fe_5Ho_3O_{12}$), iron nickel manganese oxide ($FeMnNiO_4$), γ-iron oxide (maghemite), iron oxide (magnetite), α-iron oxide (hematite), lanthanum ferrite ($FeLaO_3$), magnesium ferrite ($MgFe_2O_4$), manganese ferrite ($Fe_2MnO_4$), manganese dioxide ($MnO_2$), neodymium ditianate ($Nd_2O_7Ti_2$), aluminum nickel ferrite ($Al_{0.2}Fe_{1.8}NiO_4$), nickel-zinc ferrite ($Fe_2Ni_{0.5}O_4Zn_{0.5}$), nickel zinc ferrite ($Fe_2Ni_{0.4}Zn_{0.6}$), nickel zinc ferrite ($Fe_2Ni_{0.8}O_4Zn_{0.2}$), nickel (II) oxide (NiO), nickel ferrite ($Fe_2NiO_4$), samarium ferrogarnet ($Fe_5O_{12}Sm_3$), silver lanthan ferrite ($Ag_{0.5}Fe_{12}La_{0.5}O_{19}$), yttrium iron garnet ($Fe_5O_{12}Y_3$), yttrium orthoferrite ($FeO_3Y$), said starting material being subdivided to yield a plurality of aggregable, smaller sized particles, suspended in a liquid medium and contacted with said coating material to form a mixture, before substantial aggregation of said particles occurs, the improvement which comprises heating the mixture to a temperature of at least about 45° C. for a time sufficient for said coating material to adhere to said substrate.

2. The improved process according to claim 1, wherein said heating is carried out at a temperature from about 60° C. to about 85° C.

3. The improved process according to claim 1, wherein the liquid mixture is an aqueous suspension.

4. The improved process according to claim 1, wherein the coating material is a natural or synthetic polymer.

5. The improved process according to claim 1, wherein the coating material is a polypeptide, a protein, or an antibody.

6. The improved process according to claim 1, wherein said particulate magnetic starting material is subdivided under the influence of irradiation, vibration, pH modification, sonication, or a combination thereof.

7. The improved process according to claim 1, wherein said particulate magnetic starting material is subdivided by sonication.

8. The improved process according to claim 1, wherein said coated magnetic particles generally have a maximum dimension of less than $0.2\mu$.

9. The improved process according to claim 1, wherein said coated magnetic particles have a maximum dimension of less than $0.1\mu$.

10. The improved process according to claim 1, wherein the weight ratio of said particulate magnetic substrate to said coating material is from about 1000:1 to about 1:10.

11. The improved process according to claim 1, including the further step of recovering said resuspendable coated particles by high gradient magnetic separation.

12. The improved process according to claim 1, further comprising resuspending the magnetic coated particles in water or an aqueous buffer solution.

13. The improved process according to claim 12, wherein said resuspension is conducted under the influence of sonication.

14. The improved process according to claim 1, wherein said particulate magnetic starting material is subdivided in the presence of said coating material, without application of heat and thereafter heating said coated magnetic particles.

15. The improved process according to claim 1, wherein said particulate magnetic starting material is subdivided in the presence of said coating material, at a temperature in the range of about 50° C. to about 85° C.

16. The improved process according to claim 1, wherein said particulate magnetic starting material is subdivided in the substantial absence of said coating material, without application of heat, and said coated magnetic particles are subsequently heated.

17. The improved process according to claim 1, wherein said particulate magnetic starting material is subdivided in the substantial absence of said coating material, without application of heat, and said subdivided starting material and said coating material are thereafter contacted with application of heat.

18. The improved process according to claim 1, wherein said particulate magnetic starting material is subdivided in the substantial absence of said coating material, at a temperature in the range of about 0° C. to about 30° C., and said heated, subdivided starting material and said coating material are thereafter contacted with application of heat.

19. Resuspendable coated magnetic particles prepared by the process of claim 1.

20. A process for making a stable suspension of resuspendable magnetic particles, said process comprising:

(a) forming a liquid mixture of a particulate, magnetic, transition metal oxide starting material selected from the group consisting of chromium (IV) oxide ($CrO_2$), cobalt ferrite ($CoFe_2O_4$), copper ferrite ($CuFe_2O_4$), dysprosium ferrogarnet ($DyFe_5O_{12}$), dysprosium orthoferrite ($Dy_4FeO_3$), erbium orthoferrite ($ErFeO_3$), gadolinium ferrogarnet ($Fe_5Gd_3O_{12}$), holmium iron garnet, ($Fe_5Ho_3O_{12}$), iron nickel manganese oxide ($FeMnNiO_4$), γ-iron oxide (maghemite), iron oxide magnetite, α-iron oxide (hematite), lanthanum ferrite ($FeLaO_3$), magnesium ferrite ($MgFe_2O_4$), manganese ferrite ($Fe_2MnO_4$), manganese dioxide ($MnO_2$), neodymium dititanate ($Nd_2O_4Ti_2$), aluminum nickel ferrite ($Al_{0.2}Fe_{1.8}NiO_4$), nickel-zinc ferrite ($Fe_2Ni_{0.5}O_4Zn_{0.5}$), nickel zinc ferrite ($Fe_2Ni_{0.4}Zn_{0.6}$), nickel zinc ferrite ($Fe_2Ni_{0.8}O_4Zn_{0.2}$), nickel (II) oxide (NiO), nickel ferrite ($Fe_2NiO_4$), samarium ferrogarnet ($Fe_5O_{12}Sm_3$), silver lanthan ferrite ($Ag_{0.5}Fe_{12}La_{0.5}O_{19}$), yttrium iron garnet ($Fe_5O_{12}Y_3$), yttrium orthoferrite ($FeO_3Y$);

(b) sonicating said mixture to subdivide said particulate magnetic starting material into a plurality of uncoated aggregable, smaller sized particles suspended in said liquid at a temperature of about 75° C., for time sufficient to produce particles in the size range of 40–180 nm;

(c) contacting said heating, uncoated suspended smaller sized particles with said coating material, before substantial aggregation of said smaller sized particles occurs, at a temperature in the range of 70° C.–80° C. for a time sufficient for said coating material to adhere to said smaller sized particles, thereby forming a stable suspension of said resuspendable, coated magnetic particles.

21. Resuspendable coated magnetic particles prepared by the process of claim 20.

22. A resuspendable coated magnetic, transition metal oxide particle exhibiting colloidal stability in a 1 molar salt solution, as indicated by an increase in particle size of no greater than two-fold upon exposure of said particle to said salt solution for a period of up to 24 hours at room temperature.

23. The process according to claim 20, wherein said coating material is selected from the group consisting of protein, peptide and nucleic acid.

* * * * *